United States Patent [19]

Yoshida

[11] Patent Number: Plant 7,744

[45] Date of Patent: Dec. 10, 1991

[54] AFRICAN VIOLET NAMED 'AGNES'

[76] Inventor: Eiichi Yoshida, P.O. Box 4836, Hayward, Calif. 94540-4836

[21] Appl. No.: 524,126

[22] Filed: May 14, 1990

[51] Int. Cl.[5] ..... A01H 5/00

[52] U.S. Cl. ..... Plt./69

[58] Field of Search ..... Plt./69

*Primary Examiner*—James R. Feyrer

[57] ABSTRACT

A new variety of African violet plant for potted plant culture particularly distinguished by its year 'round blooming capability, its profuse production of blooms in cluster like a nosegay, and its compact growth with abundant foliage of solid green color which provides a spreading base for the blossoms.

1 Drawing Sheet

BACKGROUND OF THE NEW PLANT

This new variety of African violet plant was obtained by cross-pollenating the seed parent "Melodie" Mary×Holtkamp XX/79 and the pollen parent "Melodie" Mitzi Sport. The seed pods of the pollenated plants were used as the generic basis for initiating further propagation trials. A total of 700 seedlings resulted from the stated cross. Of these, 16 individual seedlings were selected and retained for further observation to assess vigor, early development, early blooming, and bloom character; the mature characteristics of growth habit; and, for testing to reflect diease resistance of the selections.

The specified plant was a selection from among the 16 plants remaining from the initial cross. The plant of this disclosure was selected based on a number of outstanding characteristics including attractive, quality plant confirmation with starkly contrasting top and bottom leaf coloration with some mature leaves having gentle undulations and the generous and central placement of single flowers of attractive, rounded shape with ruffled petal outer portions, moderately deep violet petals which appealingly contrast with bright yellow, conspicuous anthers, and was subsequently denominated 'Agnes'.

I have asexually reproduced 'Agnes' by taking leaf cuttings to start plants in the usual way for *Saintpaulia ionantha.* Descendants of this original selection have proven to be completely the same as the parent plant in all distinguishing characteristics to establish that 'Agnes' is stable.

BRIEF DESCRIPTION OF THE DRAWING

Sheet one is a full color photograph view of the plant in bloom, the colors shown being as nearly true as it is reasonably possible to obtain by conventional photographic procedures.

DESCRIPTION OF THE PLANT

The following is a detailed description of my new Afrian violet with the color designation being accorded to the R.H.S. Colour Chart published by The Royal Horticultural Society of London, England, with collaboration by The British Colour Council.

THE PLANT

Name: Agnes.
Origin: Seedling.
Parentage:
- *Seed parent.*—Saintpaulia Melodie Mary×Holtkamp XX/79.
- *Pollen parent.*—Saintpaulia Melodie Mitzi Sport.

Classification:
- *Botanic.*—*Saintpaulia ionantha.*
- *Commercial.*—African violet.

Form: Rosette arrangement.
Height: 8 to 10 cm.
Growth: Moderate, petioles at first upright, becoming horizontal with age.
Size: Medium, to 20 cm. in diameter.
Mutation prone: None observed for flowers or foliage.
Foliage:
- *Shape.*—Ovate, slight cordate base, rounded tip, slight crenate margin.
- *Length.*—7 to 8 cm. on mature leaves.
- *Width.*—6 to 7 cm. on mature leaves.
- *Color.*—Upperside: Medium green. Underside: Pale green.
- *Texture.*—Upperside: Pubescent. Underside: Puberulent.
- *Ribs and veins.*—Pronounced, pinnate, red pigmented on underside.
- *Petiole.*—Flattened above, pubescent, red pigmented.

THE FLOWER

Blooming habit: Continuous and abundant under optimal growing conditions.
Number: 10 to 15 per peduncle.
Size of flower: 3 to 4 cm. in diameter.
Color: Violet-Blue R.H.S. 89A.
Type: Single, violet-like.
Petals: Five, margins ruffled.
Texture: Smooth, slightly flexible.
Appearance: Upperside glabrous, lower side slightly puberulent.
Peduncles: 6 to 7 cm. in height, pubescent, red pigmented.
Inflorescence: Cyme, upright, above the foliage.
Calyx: Quinquepartite, red pigmented, puberulent.
Persistence: Flowers do not drop.
Fragrance: None.

REPRODUCTIVE ORGANS

Stamen: Two per flower.

*Anthers.*—Bright Yellow, basifixed, two per filament.

*Filaments.*—c. 0.4 cm. in length.

*Pollen.*—Light Yellow.

Pistils: One.

*Stigma.*—Visible and accessible, becoming swollen when receptive and exuding a droplet of clear liquid.

*Style.*—c. 0.7 cm. in length.

*Ovary.*—Superior.

I claim:

1. A new and distinct cultivar of African violet named 'Agnes', as described and illustrated, and particularly characterized by it profuse deep violet-blue flowers, upright flower stems, vigorous growth habit, flowering 11 to 12 weeks after potting and its long lasting and non-dropping flowers which give the plant a substantially continuous beauty.

* * * * *

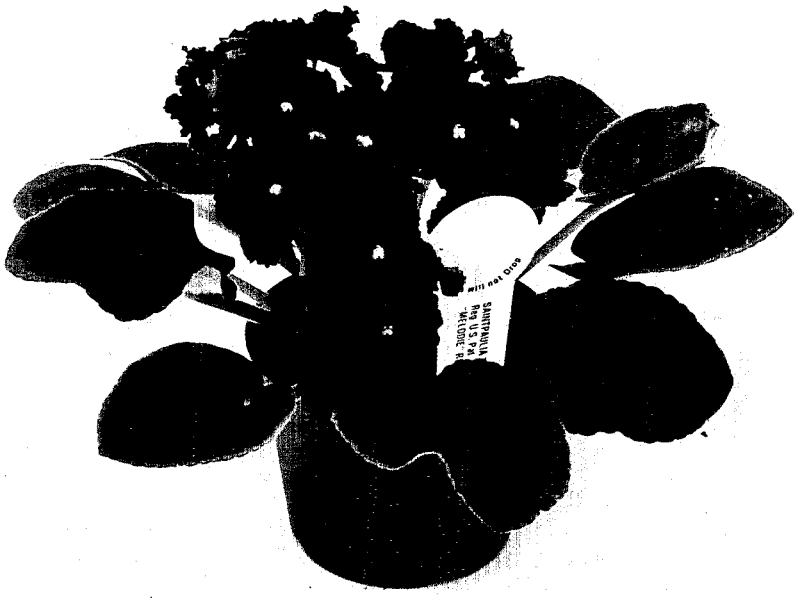
SANTPAULIA
Pat. U.S. Pat. No.
"MELODIE"
DO NOT DUG
WITH